(12) United States Patent
Holladay

(10) Patent No.: US 7,926,948 B2
(45) Date of Patent: Apr. 19, 2011

(54) ASTIGMATIC AXIS INDEPENDENT SPATIAL FREQUENCY AND CONTRAST SENSITIVITY TARGET AND METHOD

(75) Inventor: Jack T. Holladay, Bellaire, TX (US)

(73) Assignee: M&S Technologies, Inc., Park Ridge, IL (US)

( * ) Notice: Subject to any disclaimer, the term of this patent is extended or adjusted under 35 U.S.C. 154(b) by 0 days.

(21) Appl. No.: 12/098,874

(22) Filed: Apr. 7, 2008

(65) Prior Publication Data

US 2008/0186450 A1 Aug. 7, 2008

Related U.S. Application Data

(63) Continuation of application No. 10/694,609, filed on Oct. 27, 2003, now Pat. No. 7,354,155.

(60) Provisional application No. 60/422,084, filed on Oct. 29, 2002.

(51) Int. Cl.
*A61B 3/02* (2006.01)
*A61B 3/00* (2006.01)
(52) U.S. Cl. ........................ 351/239; 351/246
(58) Field of Classification Search .......... 351/205–246
See application file for complete search history.

(56) References Cited

U.S. PATENT DOCUMENTS

| 3,993,976 | A | | 11/1976 | Ginsburg | |
|---|---|---|---|---|---|
| 4,257,690 | A | | 3/1981 | Howland | |
| 4,365,873 | A | * | 12/1982 | Ginsburg | 351/239 |
| 4,426,663 | A | | 1/1984 | Evans et al. | |
| 4,448,486 | A | | 5/1984 | Evans | |
| 4,453,804 | A | | 6/1984 | Evans | |
| 4,789,234 | A | | 12/1988 | Ginsburg et al. | |
| 4,800,404 | A | | 1/1989 | Ginsburg et al. | |
| 4,859,052 | A | | 8/1989 | McFarland et al. | |
| 5,054,908 | A | | 10/1991 | Katsumi et al. | |
| 5,078,486 | A | | 1/1992 | Evans | |
| 5,216,458 | A | | 6/1993 | Andera et al. | |
| 5,414,479 | A | | 5/1995 | Ginsburg | |
| 5,500,699 | A | | 3/1996 | Ginsburg | |
| 5,552,842 | A | | 9/1996 | Ginsburg et al. | |
| 5,969,792 | A | | 10/1999 | Ginsburg | |
| 6,623,118 | B2 | | 9/2003 | De La Rosa | |
| 6,926,408 | B2 | | 8/2005 | Sarver | |
| 7,354,155 | B2 | * | 4/2008 | Holladay | 351/239 |
| 7,367,675 | B2 | * | 5/2008 | Maddalena et al. | 351/237 |
| 2004/0105073 | A1 | | 6/2004 | Maddalena et al. | |

* cited by examiner

*Primary Examiner* — Mohammed Hasan
(74) *Attorney, Agent, or Firm* — Fay Sharpe LLP

(57) ABSTRACT

A set of visual targets and a method for using these targets to evaluate the spatial frequency response and contrast sensitivity of the human visual system. The invention includes four choice test, six choice test, sinusoidal bulls eye and fundamental sinusoidal letters or optotype targets. The four and six choice targets feature sinusoidal gratings oriented vertically, horizontally and at angles thereto. The sinusoidal bull's eye target features concentric circular light and dark areas with brightness varying in a radial sinusoidal fashion. The fundamental sinusoidal optotype target features an optotype, such as a letter, that is made up of strokes, each of which have a width that is equal to ½ of a single sinusoidal period.

5 Claims, 3 Drawing Sheets

"SEABURST"     "CLOCK"     LANCASTER "CROSS"

ASTIGMATIC AXIS INDEPENDENT SPATIAL FREQUENCY AND CONTRAST SENSITIVITY TARGET AND METHOD

CLAIM OF PRIORITY

This application is a continuation application of U.S. Ser. No. 10/694,609, filed Oct. 27, 2003, now U.S. Pat. No. 7,354,155 B2 which claims priority from U.S. Provisional Patent Application Ser. No. 60/422,084, filed Oct. 29, 2002, the disclosures of which are hereby incorporated by reference.

BACKGROUND OF THE INVENTION

Prior art charts and targets, such as those illustrated in U.S. Pat. Nos. 5,500,699 and 5,414,479 to Ginsburg, yield variable results depending on the axis of residual astigmatism and higher order aberrations such as vertical coma and other non-rotationally symmetric aberrations. More specifically, prior targets used for measuring contrast sensitivity and spatial frequency response in their preferred embodiment have rows and columns of patches that are presented against a white background. The targets are comprised of patches (~1.4° of solid viewing angle) of gratings having successive parallel aligned light and dark areas, which parallel aligned light and dark areas have substantially linear character with the contrast levels and/or spatial frequency or size. These gratings are oriented vertically and at ±15° of vertical (left of vertical, vertical and right of vertical) resulting in "three choice test" (three forced choices). The spatial frequencies covered by the targets may range from 0.5 to 64 cycles per degree (CPD), but typically the values have been L5, 3, 6, 12 and 18 CPD. The patient is asked to identify the direction of the lines (left of vertical, vertical and right of vertical). The lowest contrast level that each spatial frequency is correctly identified is considered the contrast threshold from which the contrast sensitivity is determined.

Contrast sensitivity testing and spatial frequency response may be performed with a patient's best refraction (spectacles, contacts lenses, etc.) or with no correction in place. The need for taking these measurements with or without refractions has become extremely important in determining the visual outcomes from refractive surgery {radial keratotomy, Photorefractive Keratectomy (PRK) and Laser Assisted Keratomillieusis in Situ (LASIK) and phakic intraocular lenses}.

The problem with the current embodiment of the targets is that they are spatially biased in one direction (usually vertical or near vertical). Refractive errors such as astigmatism and higher order aberrations (coma, trefoil, tetrafoil, ) cause lines to appear darker (higher contrast) in one angular orientation than in the orthogonal orientation where they appear much lighter (lower contrast). In fact, the finding that lines appear darker in one meridian than another is used to determine the axis (orientation) of the astigmatism and higher order aberrations. The Lancaster Wheel and Sunburst target (FIG. 1A & B) are examples of these tests. In FIG. 1A, the actual appearance of the target is with all radial lines appearing equally dark. With astigmatism and non-rotationally symmetric higher order vertical aberrations the lines appear darker (higher contrast) in the meridian nearest the retina and lighter (lower contrast) in the orthogonal meridian, as shown in FIG. 1B.

Astigmatism simply means the power of the eye is similar to a torus, biconic or toric ellipsoid where there is a strong and a weak power that are 90° apart. In FIG. 1B, the darkest line in the Clock pattern is along the meridian that is 2 o'clock (30° from horizontal). The lightest line is 90° away at 11 o'clock. A patient with astigmatism oriented at 30° would see the sunburst with this appearance. Astigmatism can occur at any axis, so the appearance of the Sunburst or Clock pattern will appear differently depending on the amount and orientation of the astigmatism. Astigmatism is one of the simplest of optical errors and is therefore considered to be Lower Order Aberration optically and can be corrected with spectacles. Higher order aberrations of the eye can occur also (coma, trefoil, tetrafoil, . . . ) which are more complex aberrations of the optical system that cannot be corrected with spectacles. They do however, cause the Sunburst pattern to have irregularly darker and lighter spokes. Depending on the exact aberrations of the individual, vertical or near vertical lines will appear differently to each individual causing a difference in the threshold of the contrast of the actual lines seen.

The astigmatic patient with a vertical focal line nearer the retina will see the vertical gratings at a much higher contrast than a person with a horizontal focal line nearer the retina. The result is that the orientations of the astigmatism and non-rotationally higher order aberrations have a direct impact on the results of the contrast sensitivity test and the spatial frequency response. This should not occur. The axis of astigmatism and orientation of symmetric higher order aberrations should have no impact on the contrast sensitivity or spatial frequency response. The method to follow using linear gratings at other orientations, the new "rotationally" symmetric target ("Sinusoidal Bull's Eye" target) and the "fundamental sinusoidal" letters eliminate or reduce any effect of non-rotational refractive errors (low and higher order aberrations).

Aberrations such as astigmatism and other higher order aberrations can make the contrast of the lines vary by large contrast amounts (greater than 50% difference in contrast). Because the appearance of the target contrast to the patient is reduced by the aberrations, the results of the contrast threshold are variable and depend of the orientation of the aberration.

SUMMARY OF INVENTION

The invention is a set of visual targets and method of using these targets to evaluate the spatial frequency response and contrast sensitivity of the human visual system. The invention is an improvement over prior art charts and targets, such as those presented in U.S. Pat. Nos. 5,500,699 and 5,414,479 to Ginsburg. The previous charts and targets yield variable results depending on the axis of astigmatism and rotational orientation and higher order aberrations such as vertical coma and other non-rotationally symmetric aberrations (FIG. 1B).

The invention includes, but is not limited to, Four Choice Test, Six Choice Test, Rotationally Symmetric (Sinusoidal Bull's Eye) Target Test and Fundamental Sinusoidal Letters or Optotype embodiments. The Four Choice Test has sinusoidal gratings oriented at four different meridians, each separated by 45°. Having these four orientations and presenting them randomly will "average out" any bias due to the orientation of the astigmatism, because there is no overall bias in the orientation of the targets (not all vertical or near vertical).

The Six Choice Test has sinusoidal gratings oriented at six different meridians, each separated by 30°. Having these six orientations and presenting them randomly will "average out" any bias due to the orientation of the astigmatism, because there is no overall bias in the orientation of the targets (not all vertical or near vertical). The Six Choice "Test is superior to the Four Choice Test in that the patient has only a 1 in 6 chance of guessing (false positive) as opposed to 1 in 4. The disadvantage is the test requires more presentation and therefore requires more time.

The Sinusoidal Bull's Eye has a spatial frequency that is the same as linear gratings, but the target is rotationally symmetric. Patients with astigmatism and other non-rotationally symmetric aberrations will have no advantage or disadvantage in the appearance of the target. For two patients with the same amount (magnitude) of astigmatism, but at different orientations, the target will appear the same, only rotated. The result is no difference in the apparent contrast of the target.

The Fundamental Sinusoidal Letters are comprised of sinusoidal elements or "strokes"[9] that can make the 26 letters of the Arabic alphabet. Although Sloan has shown that 10 of these letters (D, K, R, H, V, C, N, Z, S, O) have the same difficulty for recognition the technique may be used for any letters or symbols that can be made with multiple segments (strokes or elements) in any language [Ref 1: Sloan, L, Rowland W M and Altaian A. Comparison of three types of test target for the measurement of visual acuity. Q. Rev. Ophthal. 8:4-16 (1952). Ref. 2: Recommended Standard Procedures for the Clinical Measurement and Specification of Visual Acuity. Report of Working Group 39. Adv. Ophthal. Vol. 41, pp. 103-148 (Karger, Basel 1980).] Although some letters may have a slight directional bias for astigmatism, the use of multiple letters averages out any bias, similar to standard visual acuity testing. The Fundamental Sinusoidal Optotype is not limited to letters, but may be used-for any other optotype or symbol used in visual acuity or contrast sensitivity testing.

For a more complete understanding of the nature and scope of the invention, reference may now be had to the following detailed description of embodiments thereof taken in conjunction with the appended claims and accompanying drawings.]

DESCRIPTION OF THE PREFERRED EMBODIMENTS

As a prelude to a description of the invention and its embodiments, it is helpful to present the following definitions so that the concepts set forth therein may be more readily understood. It should be noted that the terms "chart" and "target" are used interchangeably throughout the following description.

Meridians and Semi-meridians: A meridian is any diameter through the center of a circle. A semi-meridian is any radius. Clock hours are semi-meridians and meridians would be pairs of semi-meridians (9-3, 10-4, 11-5, . . . . The semi-meridians may also be described in degrees where each clock hour is 30°. The 3 o'clock semi-meridian is considered zero degrees and the angle increases positively in a counter-clockwise manner as in a standard polar coordinate system.

Contrast Levels: The contrast between two adjacent brightnesses is defined as the difference in the brightnesses divided by the sum of the brightnesses. For example, a projected target may have a 98 lux brightness at the peak level and 2 lux brightness in the dark area, the contrast is (98−2)/(98+2) =96% contrast. Because the visual system responds exponentially to contrast, contrast levels are often given in common log units. Therefore, zero log units is 100% contrast, −1 log units is 10% contrast, −2 log units is 1% contrast and −3 log units is 0.1% contrast. The normal human contrast threshold is within this range. Sometimes Octave steps (doubling) are used, which is equivalent to −0.301 log units change in contrast. Decibels (dB) may also be used. A decibel is ten times the log unit. Therefore, −0.301 log units is equivalent to −3.01 dB.

Spatial frequency: Spatial frequency is the number of times that a cycle is repeated over a given distance. Distances are measured using the visual angle, so the unit of measure is usually in cycles (number of sinusoids) that occur in a single degree. For example, 30 cycles per degree, means that the sinusoidal pattern is repeated 30 times in an angle of 1 degree. For the Fundamental Sinusoidal letters, each stroke is considered to be ½ the fundamental sinusoidal period. For 30 cycles per degree, the width of each stroke of a letter would be 1/60 of a degree and the height and length of each letter would be equal and 5 times larger than the width of a stroke, as is the standard for letters used in visual acuity testing (previous 2 references).

Figure 1A:
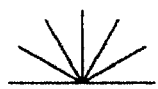
FIG. 1A illustrates Sunburst, Clock (or Wheel) and Lancaster Cross prior art targets.
Figure 1A:
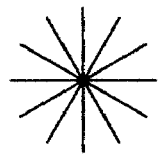
Figure 1A:
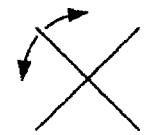

With reference to FIG. 1A, the Sunburst, Wheel and Lancaster cross are all examples of radial lines emanating from a point. When a patient has astigmatism or higher order non-rotationally symmetric aberration, the lines will no longer appear equally dark.

Figure 1B:
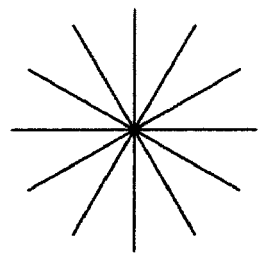
FIG. 1B illustrates the appearance of the prior art Wheel target to a patient having astigmatism at 30°.

The appearance of the Wheel to a person with astigmatism at 30° is presented in FIG. 1B. If a patient's astigmatism were at 60°, the 1 o'clock line would appear darker. Although astigmatism is more commonly vertical when people are young and horizontal when people are old, astigmatism can occur at any orientation in the human population. The present invention overcomes the disadvantages of prior art charts and targets described with reference to FIGS. 1A and 1B.

Figure 2:
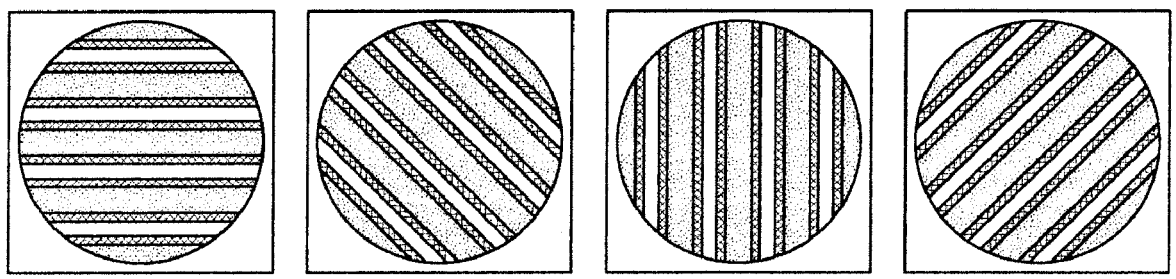
FIG. 2 illustrates the targets of a Four Choice Test embodiment of the present invention.

Turning to FIG. 2, the first embodiment of the present invention is a Four Choice Test (4 forced choices). Rather than all targets being oriented vertically or near vertical (±15°) the four targets are oriented 45° apart (horizontally, 45°, vertically and 135°).

While the targets of the Four Choice Test embodiment of the present invention, at multiple spatial frequencies and contrast levels, may be combined on a single wall chart, in the fashion illustrated in U.S. Pat. No. 5,500,699 to Ginsburg, for example, the preferred form of creation and display of the targets is one at a time by software on the screen of a computer monitor, More specifically, a patient sits and faces the monitor. As an example, for a monitor having an approximately 15" to 60" diagonal screen, with each target displayed on the monitor ranging from 1 minute of visual arc to 2° of visual arc and visual angle, the patient may sit approximately 5[?] to 30* from the screen and the ambient lighting in the room would be dark (less than 5 foot-candles).

A spatial frequency, typically the highest, is chosen by the physician (or technician) and then a target showing the highest contrast level at that frequency is displayed to the patient on the monitor. The patient then identifies the grating direction of the displayed target. This may be accomplished in a variety of ways. For example, the patient may respond verbally or click one of four buttons, with each button labeled with one of the grating directions. Successive targets for the frequency are displayed to the patient, with the directions of the gratings varied randomly, at progressively lower contrast levels. When the patient is unable to detect a target grating orientation or direction at a particular contrast level, additional targets at the same contrast level having different grating orientations are displayed. This approach is repeated as the contrast levels continue to lower. The physician records the last threshold contrast level before the patient is no longer able to identify the orientations of any of the target gratings at a particular contrast level. A second spatial frequency is selected and the above process is repeated. As an example only, five spatial frequencies may be selected for a test session having, for example, cycles of 1.5, $3_5$ 6, 12 and 24 CPD.

The Four Choice Test increases the specificity by 25% (four choices rather than three) by reducing the number of false positives (random chance of simply guessing correctly). Since the targets are equally spaced rotationally, any directional aberration (astigmatism, vertical coma and trefoil) will be averaged out by the testing. Multiple targets at the four orientations at the same spatial frequency and contrast would be required for the average to be precise.

Figure 3:
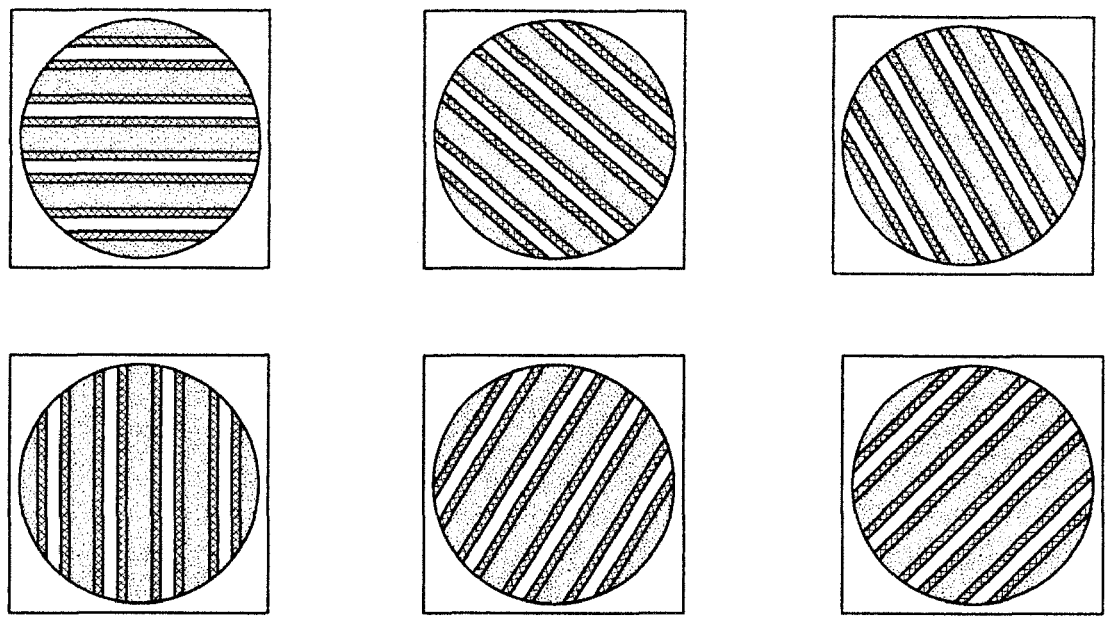
FIG. 3 illustrates the targets of a Six Choice Test embodiment of the present invention.

A second embodiment of the present invention is a Six Choice Test (6 forced choices), as shown in FIG. 3. The Six Choice Test is performed in the same manner as described above for the Four Choice Test but doubles the number of choices from the three choice test. The targets are oriented at 9-3, 10-4, 11-5, 12-6, 1-7 and 2-8 clock hours with are in 30° increments. The additional choices further increase the specificity of the test and reduce the number of false positives. The patient is asked to identify the orientation of the target by the clock hour of orientation. As with the Four Choice Test, this may be accomplished in a variety of ways. For example, the patient may respond verbally or click one of six buttons, with each button labeled with one of the grating directions.

Figure 4:
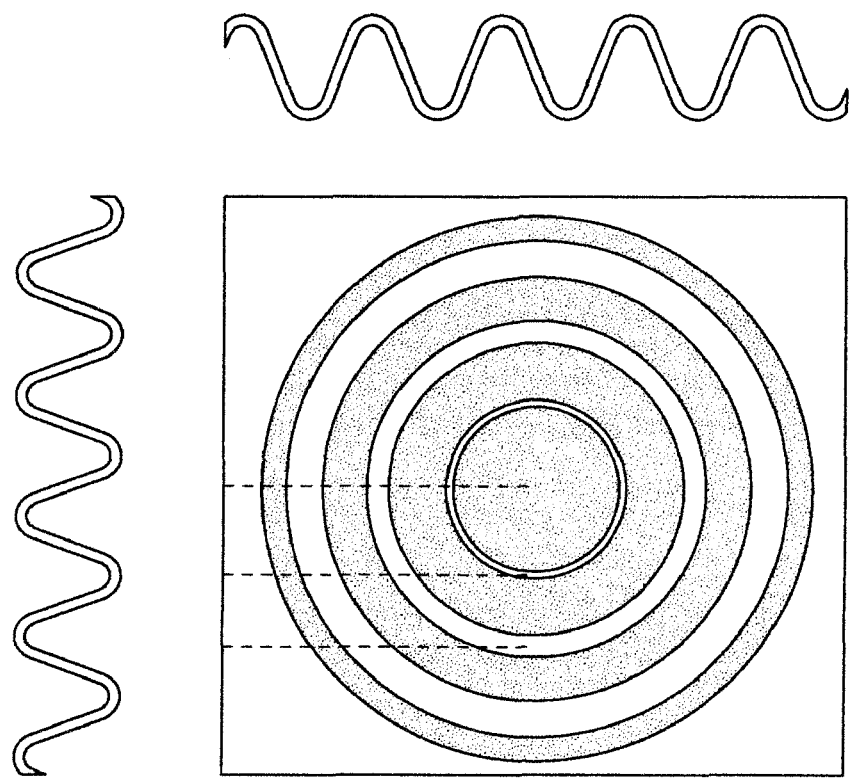
FIG. 4 illustrates a Sinusoidal Bull's Eye Target embodiment of the present invention.

A third embodiment of the present invention is a new Sinusoidal Bull's Eye (Rotationally Symmetric) Target, illustrated in FIG. 4, that eliminates the need for multiple presentations because there is no effect from the orientation of astigmatism or other non-rotational higher order aberrations. The Sinusoidal Bull's Eye Target of FIG. 4 is formed by a cross-section sinusoid that is pivoted around either the peak or valley of the sinusoid. In other words, the new target is a sinusoid rotated around a peak (center bright) or valley (center dark). Either polarity should be available. The center spot has ½ period and each (bright or dark) ring is ½ period. The fundamental spatial frequency can be for any spatial frequency. Normal human testing is usually between 0.5 and 60 cycles per degree. The rotationally symmetric nature of the sinusoidal bulls' eye target results in the light and dark areas being substantially uniform over a circumference thereof as evidenced in FIG. 4.

Figure 5:
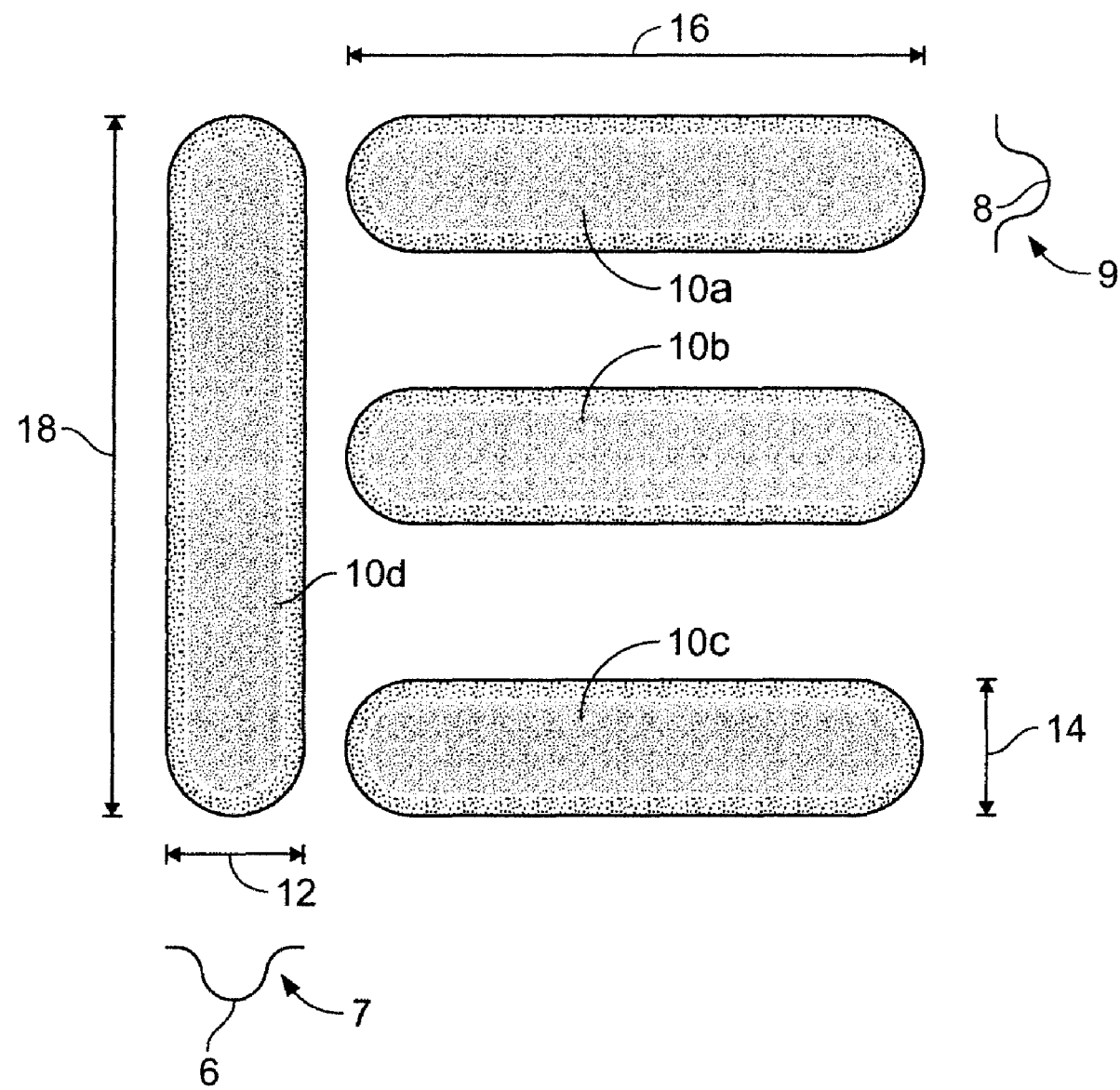
FIG. 5 illustrates a Fundamental Sinusoidal Letter Target embodiment of the present invention.

A fourth embodiment of the present invention is new Fundamental Sinusoidal Letters Target, illustrated in FIG. 5. The Fundamental Sinusoidal Letter "E" of FIG. 5 is formed by four "strokes" or elements, indicated at 10a, 10b, 10c, and 10d. It is to be understood that while only straight or linear strokes are illustrated in FIG. 5, the strokes may also be curved. Each single "stroke" or element of the letter has a central peak (center bright) or valley (center dark), illustrated at 6 for the sinusoid indicated in general at 7 and 8 for sinusoid indicated in general at 9 in FIG. 5, that tapers off in all directions sinusoidal for ½ period. Each letter is then constructed using "strokes" so that the edges of each stroke intersect at the ½ period. The fundamental spatial frequency is determined by the width of the stroke indicated at 12 and 14 in FIG. 5. The height (18 in FIG. 5) and width (12 plus 16 in FIG. 5) of the letter are equal and 5 times larger than the width of a stroke (12, 14). A Fundamental Letter equivalent to 30 cycles/degree would have a stroke width of ⅟60 of degree (1 minute of arc) width.

As an alternative to the embodiment illustrated in FIG. 5, the Fundamental Sinusoidal Optotype is not limited to letters, but may be used for any other optotype or symbol used in visual acuity or contrast sensitivity testing. The basic principle is to use the Fundamental Sinusoidal Segment (stroke or element) to construct the optotype. Using these Fundamental Sinusoidal Segments to construct an optotype or symbol eliminates higher spatial frequencies at the corners and curves, which has been a criticism of using letters (or other complex optotypes) for contrast sensitivity or standard visual acuity testing. Any optotype, symbol or letter constructed in this matter eliminating the higher spatial frequencies and providing "pure" spatial frequency result at any spatial frequency.

As with the Four and Six Choice Tests, the targets of FIG. 4 and 5 are preferably presented to the patient on a computer screen, but may also be displayed on a chart or slide, after an initial spatial frequency is selected by the physician. Furthermore, as with the Four and Six Choice Tests, successive targets are presented to the patient, each target having a progressively lower contrast level. A control disk, however, is randomly displayed to the patient in place of the target of FIG. 4. The control disk is a gray disk of the same diameter as the Sinusoidal Bull's Eye Target. The gray disk would be the same as the MEAN brightness of the Sinusoidal Bull's Eye Target. The test would be a "forced two choice". "Do you see a Bull's Eye or a Gray Disk?" The patient may answer in a variety of ways such as by a verbal response or clicking one of two buttons where one button is labeled "Yes, Bull's Eye is present" and the other button is labeled "No, Bull's Eye is NOT present, it is a gray disk." In the case of FIG. 5, the patient would be asked to identify or "name" the optotype that is being displayed. The patient may answer in a variety of ways such as by a verbal response or by clicking a button corresponding to the letter or other optotype or, if the optotype is not seen, by clicking a button that is labeled "No optotype is present." When the patient is no longer able to detect the Bull's Eve, or identify the optotype, the physician writes down the last threshold contrast level that was repeatable. This test is the best for "automated" display on the computer monitor because there are only two choices so it goes very fast. With big steps, little steps and double checks of the threshold level reported.

It should be noted that, in addition to the preferred method of displaying the targets on a computer screen, the various targets of the embodiments of the invention described above may be created and displayed in any way known in the prior art including, but not limited to, projection onto a screen, printing on paper or the like and/or displaying on a high definition television system.

While the preferred embodiments of the invention have been shown and described, it will be apparent to those skilled in the art that changes and modifications may be made therein without departing from the spirit of the invention, the scope of which is defined by the appended claims.

What is claimed is:

1. A set of targets operatively configured for display on a computer monitor for testing spatial frequency and contrast sensitivity comprising:

a) a plurality of substantially sinusoidal bull's eye targets, each featuring concentric circular light and dark areas with brightness in the concentric circular light and dark areas varying in a substantially sinusoidal fashion; and b) each of said plurality of substantially sinusoidal bull's eye targets having a unique combination of spatial frequency and contrast level.

2. A fundamental substantially sinusoidal optotype target operatively configured for display on a computer monitor for testing spatial frequency and contrast sensitivity comprising an optotype constructed entirely from a plurality of strokes, where each of said strokes features a width equal to substantially a single sinusoidal period and a length that is substantially a multiple of the width.

3. The fundamental substantially sinusoidal optotype target of claim 2 wherein the optotype is a letter.

4. The fundamental substantially sinusoidal optotype target of claim 2 wherein the optotype features a width and a length that are equal to each other and five times the stroke width.

5. A method of testing spatial frequency and contrast sensitivity comprising the steps of:

a) providing a plurality of substantially sinusoidal bull's eye targets having concentric circular light and dark areas with brightness in the concentric circular light and dark areas varying in a substantially sinusoidal fashion, the light and dark areas being substantially uniform over a circumference thereof, and each of said targets having a unique combination of spatial frequency and contrast level;

b) providing a control;

c) displaying on a computer monitor one of said substantially sinusoidal bull's eye targets to a patient;

d) asking the patient if he sees the substantially sinusoidal bull's eye target;

e) displaying the control; and f) asking the patient if he sees the substantially sinusoidal bull's eye target.

* * * * *